United States Patent
Beidler et al.

(10) Patent No.: US 8,613,921 B2
(45) Date of Patent: Dec. 24, 2013

(54) ANTIBODIES THAT BIND TGF-ALPHA AND EPIREGULIN

(75) Inventors: Catherine Brautigam Beidler, Poway, CA (US); Josef George Heuer, Carmel, IN (US); Ramona Judita Petrovan, San Diego, CA (US)

(73) Assignee: Eli Lilly and Company, Indianapolis, IN (US)

( * ) Notice: Subject to any disclaimer, the term of this patent is extended or adjusted under 35 U.S.C. 154(b) by 64 days.

(21) Appl. No.: 13/432,204

(22) Filed: Mar. 28, 2012

(65) Prior Publication Data

US 2012/0258109 A1 Oct. 11, 2012

Related U.S. Application Data

(60) Provisional application No. 61/472,338, filed on Apr. 6, 2011.

(51) Int. Cl.
*A61K 39/395* (2006.01)
*C07K 14/495* (2006.01)
*C07K 14/475* (2006.01)
*C07K 14/71* (2006.01)

(52) U.S. Cl.
USPC ............ 424/136.1; 424/139.1; 514/15.4

(58) Field of Classification Search
None
See application file for complete search history.

(56) References Cited

U.S. PATENT DOCUMENTS

| 5,190,858 A | 3/1993 | Sorvillo |
|---|---|---|
| 2009/0324491 A1 | 12/2009 | Aburatani et al. |
| 2010/0111965 A1 | 5/2010 | Johnston et al. |
| 2011/0150886 A1 | 6/2011 | Caswell et al. |
| 2012/0141501 A1* | 6/2012 | Yoshida et al. |

FOREIGN PATENT DOCUMENTS

| WO | 2008044068 | 4/2008 |
|---|---|---|
| WO | 2009127881 | 10/2009 |
| WO | 2010/137654 A1 | 12/2010 |

OTHER PUBLICATIONS

Modjtahedi, H., et al., "Anti-EGFR monoclonal antibodies which act as EGF, TGF.alpha., HB-EGF and BTC antagonists block the binding of epiregulin to EGFR-expressing tumours," Int. J. Cancer 75(2):310-316, 1998.*

Tesch et al., Recent insights into diabetic renal injury from the db/db mouse model of type 2 diabetic nephropathy, Am. J. Physiol. Renal Physiol. 200:F301-F310, 2011.*

Terzi, et al., A central role of EGFR transactivation in chronic kidney diseases, Drug Discovery Today: Disease Mechanisms, vol. 4, No. 1, Mar. 2007.

Usha, Panchapakesan, Renal epidermal growth factor receptor: Its role in sodium and water homeostasis in diabetic nephropathy, Clinical and Experiment Pharmacology and Physiology, vol. 38, No. 2, Feb. 2011.

Lautrette, Alexandre, Angiotension II and EGF Receptor Cross—Talk in Chronic Kidney Diseases: A New Therapeutic Approach, Nature Medicine, vol. 11, No. 8, Aug. 2005, pp. 867-874.

Laouari, Denise. TGF-alpha Mediates Genetic Susceptibility to Chronic Kidney Disease, J. Am. Soc. Nephrol. 22, pp. 327-335, Dec. 23, 2010.

* cited by examiner

*Primary Examiner* — Claire Kaufman

(74) *Attorney, Agent, or Firm* — Robert B. Johnson; Andrea M. Castetter

(57) ABSTRACT

The present invention provides antibodies that bind human TGF-alpha and human Epiregulin and are characterized as having high affinity, selective, and strong neutralizing properties. The antibodies are useful in the treatment of diabetic nephropathy.

14 Claims, No Drawings

ANTIBODIES THAT BIND TGF-ALPHA AND EPIREGULIN

The present invention relates to antibodies that bind human TGF-alpha and Epiregulin and uses thereof.

TGF-alpha and Epiregulin are two of seven ligands of the Epidermal Growth Factor Receptor ("EGFR") that normally function in wound healing following injury. Diabetic nephropathy ("DN") is a major diabetic complication and is the leading cause of end stage renal disease ("ESRD"). Proteinuria is a clinical marker of renal functional decline accompanying DN and is associated with disease progression and increased cardiovascular risk, such as heart failure, vascular disease, dysrhythmia. The standard of care for DN includes ACE inhibitors and angiotensin receptor blockers ("ARBs") that only slow disease progression and leave considerable residual risk.

Blocking the EGFR attenuates not only proteinuria, but also renal pathology in preclinical animal models of renal disease. However, EGFR inhibitors, such as ERBITUX®, while approved for cancer, are associated with side effects such as a severe skin rash on the face and shoulders associated with target inhibition in the skin. Thus, there is still a need for alternative therapies for DN. In addition, there is a need for a more effective treatment therapy for DN.

Antibodies that bind TGF-alpha have been described (for example, see U.S. Pat. No. 5,190,858). In addition, antibodies that bind Epiregulin have been described (for example, see US 2009/0324491).

The present invention provides antibodies against TGF-alpha and Epiregulin for the treatment of DN. Furthermore, the present invention provides antibodies against TGF-alpha and Epiregulin that engage the target in vivo and subsequently cause a reduction in proteinuria with a concomitant reduction in disease progression and cardiovascular risk.

The present invention provides therapeutically useful antibodies that bind both TGF-alpha and Epiregulin that possess a number of desirable properties. The antibodies of the present invention have high affinity and are selective with full neutralizing activity against human TGF-alpha and human Epiregulin. When administered, the antibodies of the present invention also result in a decrease in albuminuria and in renal pathology for tubular protein, interstitial fibrosis, mesangial matrix expansion, and pelvic dilation in vivo. Furthermore, the preferred antibodies of the present invention cause no observed skin toxicity associated with complete EGFR inhibition.

The present invention provides an antibody that binds TGF-alpha and Epiregulin, comprising a light chain and a heavy chain, wherein the light chain comprises a light chain variable region (LCVR) and the heavy chain comprises a heavy chain variable region (HCVR), wherein the LCVR comprises amino acid sequences LCDR1, LCDR2, and LCDR3, and the HCVR comprises amino acid sequences HCDR1, HCDR2, and HCDR3, wherein LCDR1 is SEQ ID NO:4, LCDR2 is SEQ ID NO:5, LCDR3 is SEQ ID NO:6, HCDR1 is SEQ ID NO:1, HCDR2 is SEQ ID NO:2, and HCDR3 is SEQ ID NO:3.

The present invention also provides a pharmaceutical composition comprising an antibody of the present invention, as described herein, and at least one pharmaceutically acceptable carrier, diluent, or excipient.

The present invention provides an antibody of the present invention, as described herein, for use in the treatment of diabetic nephropathy.

Throughout this disclosure, an antibody of the present invention, as described herein, binds TGF-alpha and Epiregulin, and comprises a light chain and a heavy chain, wherein the light chain comprises a light chain variable region (LCVR) and the heavy chain comprises a heavy chain variable region (HCVR), wherein the LCVR comprises amino acid sequences LCDR1, LCDR2, and LCDR3, and the HCVR comprises amino acid sequences HCDR1, HCDR2, and HCDR3, wherein LCDR1 is SEQ ID NO:4, LCDR2 is SEQ ID NO:5, LCDR3 is SEQ ID NO:6, HCDR1 is SEQ ID NO:1, HCDR2 is SEQ ID NO:2, and HCDR3 is SEQ ID NO:3.

The present invention provides an antibody, as described herein, wherein the antibody is selective to human TGF-alpha and human Epiregulin. Further, the present invention provides an antibody, as described herein, wherein the antibody has full neutralizing activity to human TGF-alpha and human Epiregulin. Further preferred, the present invention provides an antibody, as described herein, wherein the antibody is selective and has full neutralizing activity to human TGF-alpha and human Epiregulin.

The present invention provides an antibody, as described herein, wherein the antibody has a dissociation equilibrium constant, Kd, between $0.01 \times 10^{-9}$ M and $1.0 \times 10^{-9}$ M for human TGF-alpha (SEQ ID NO: 18). Further preferred, an antibody of the present invention, as described herein, has a dissociation equilibrium constant, Kd, between $0.05 \times 10^{-9}$ M and $0.8 \times 10^{-9}$ M for human TGF-alpha. The Kd values are established by a binding equilibrium at 25° C. as described in Example 2.

The present invention also provides an antibody, as described herein, wherein the antibody has a dissociation equilibrium constant, Kd, between $0.1 \times 10^{-9}$ M and $30 \times 10^{-9}$ M for met-human Epiregulin (SEQ ID NO: 22). Further preferred, an antibody of the present invention, as described herein, has a dissociation equilibrium constant, Kd, between $0.5 \times 10^{-9}$ M and $10 \times 10^{-9}$ M for human Epiregulin. The Kd values are established by a binding equilibrium at 25° C. as described in Example 2.

The present invention provides an antibody, as described herein, wherein the antibody has a dissociation equilibrium constant, Kd, between $0.01 \times 10^{-9}$ M and $1.0 \times 10^{-9}$ M for human TGF-alpha (SEQ ID NO: 18) and a Kd between $0.1 \times 10^{-9}$ M and $30 \times 10^{-9}$ M for met-human Epiregulin (SEQ ID NO: 22). Further preferred, an antibody of the present invention, as described herein, has a dissociation equilibrium constant, Kd, between $0.05 \times 10^{-9}$ M and $0.8 \times 10^{-9}$ M for human TGF-alpha and a Kd between $0.5 \times 10^{-9}$ M and $10 \times 10^{-9}$ M for human Epiregulin. The Kd values are established by a binding equilibrium at 25° C. as described in Example 2.

The present invention provides antibodies which bind human TGF-alpha and Epiregulin, and cause dose-dependent decrease in albuminuria, reduction in serum creatinine and blood urea nitrogen ("BUN") in vivo in a mouse remnant kidney model and a mouse uninephrectomy db/db model as described in Example 5 and Example 6, respectively.

The present invention provides antibodies which bind human TGF-alpha and Epiregulin, and cause reduction in renal pathology for tubular protein and interstitial fibrosis and a decrease in mesangial matrix expansion and pelvic dilation in vivo in a mouse remnant kidney model and a mouse uninephrectomy db/db model as described in Example 5 and Example 6, respectively.

The present invention provides antibodies which bind human TGF-alpha and Epiregulin, and are believed to cause a reduction in proteinuria with a concomitant reduction in disease progression and cardiovascular risk in humans. Further, the present invention provides antibodies which bind human TGF-alpha and Epiregulin, and are believed to be effective in the treatment of diabetic nephropathy in humans.

The present invention provides antibodies which bind human TGF-alpha and Epiregulin, and cause no observed skin toxicity in a toxicity study in cynomolgus monkeys as described in Example 7.

The present invention provides an antibody that binds TGF-alpha and Epiregulin, comprising a light chain and a heavy chain, wherein the light chain comprises a light chain variable region (LCVR) and the heavy chain comprises a heavy chain variable region (HCVR), wherein the LCVR comprises amino acid sequences LCDR1, LCDR2, and LCDR3, and the HCVR comprises amino acid sequences HCDR1, HCDR2, and HCDR3, wherein LCDR1 is SEQ ID NO:4, LCDR2 is SEQ ID NO:5, LCDR3 is SEQ ID NO:6, HCDR1 is SEQ ID NO:1, HCDR2 is SEQ ID NO:2, and HCDR3 is SEQ ID NO:3.

Furthermore, the present invention provides an antibody that binds TGF-alpha and Epiregulin, comprising a light chain and a heavy chain, wherein the light chain comprises a light chain variable region (LCVR) and the heavy chain comprises a heavy chain variable region (HCVR), wherein the amino acid sequence of the LCVR is SEQ ID NO: 9 or SEQ ID NO: 10.

The present invention also provides an antibody that binds TGF-alpha and Epiregulin, comprising a light chain and a heavy chain, wherein the light chain comprises a light chain variable region (LCVR) and the heavy chain comprises a heavy chain variable region (HCVR), wherein the amino acid sequence of the HCVR is SEQ ID NO: 7.

The present invention also provides an antibody that binds TGF-alpha and Epiregulin, comprising a light chain and a heavy chain, wherein the light chain comprises a light chain variable region (LCVR) and the heavy chain comprises a heavy chain variable region (HCVR), wherein an amino acid sequence of the LCVR and an amino acid sequence of the HCVR is selected from the group consisting of:
  (i) the LCVR is SEQ ID NO: 9 and the HCVR is SEQ ID NO: 7; and
  (ii) the LCVR is SEQ ID NO: 10 and the HCVR is SEQ ID NO: 7.

The present invention provides an antibody that binds TGF-alpha and Epiregulin, comprising a light chain and a heavy chain, wherein the light chain comprises a light chain variable region (LCVR) and the heavy chain comprises a heavy chain variable region (HCVR), wherein the amino acid sequence of the LCVR is SEQ ID NO: 9 and the amino acid sequence of the HCVR is SEQ ID NO: 7.

The present invention provides an antibody that binds TGF-alpha and Epiregulin, comprising a light chain and a heavy chain, wherein the light chain comprises a light chain variable region (LCVR) and the heavy chain comprises a heavy chain variable region (HCVR), wherein the amino acid sequence of the LCVR is SEQ ID NO: 10 and the amino acid sequence of the HCVR is SEQ ID NO: 7.

Furthermore, the present invention provides an antibody that binds TGF-alpha and Epiregulin, comprising a light chain and a heavy chain, wherein the amino acid sequence of the light chain is SEQ ID NO: 13 or SEQ ID NO: 14.

The present invention also provides an antibody that binds TGF-alpha and Epiregulin, comprising a light chain and a heavy chain, wherein the amino acid sequence of the heavy chain is SEQ ID NO: 12.

Furthermore, the present invention provides an antibody that binds TGF-alpha and Epiregulin, comprising a light chain and a heavy chain, wherein an amino acid sequence of the heavy chain and an amino acid sequence of the light chain is selected from the group consisting of:
  the heavy chain is SEQ ID NO: 12 and the light chain is SEQ ID NO: 13, and
  (ii) the heavy chain is SEQ ID NO: 12 and the light chain is SEQ ID NO: 14.

The present invention provides an antibody that binds TGF-alpha and Epiregulin, comprising two light chains wherein the amino acid sequence of each light chain is SEQ ID NO: 13, and two heavy chains wherein the amino acid sequence of each heavy chain is SEQ ID NO: 12.

The present invention provides an antibody that binds TGF-alpha and Epiregulin, comprising two light chains wherein the amino acid sequence of each light chain is SEQ ID NO: 14, and two heavy chains wherein the amino acid sequence of each heavy chain is SEQ ID NO: 12.

Furthermore, the present invention provides an antigen-binding fragment of an antibody, as described herein.

The present invention also provides a pharmaceutical composition comprising the antibody of the present invention, as described herein, and at least one pharmaceutically acceptable carrier, diluent, or excipient.

Furthermore, the present invention provides a pharmaceutical composition comprising the antibody of the present invention, as described herein, together with at least one pharmaceutically acceptable carrier, diluent, or excipient, and optionally other therapeutic ingredients.

The present invention also provides a method of treating diabetic nephropathy in a patient comprising administering to the patient the antibody of the present invention, as described herein.

Furthermore, the present invention provides an antibody of the present invention, as described herein, for use in therapy. Preferably, the present invention provides an antibody of the present invention, as described herein, for use in the treatment of diabetic nephropathy.

Furthermore, the present invention provides the use of an antibody of the present invention, as described herein, in the manufacture of a medicament for the treatment of diabetic nephropathy.

The present invention also provides a method of treating diabetic nephropathy in a patient comprising administering to the patient the antibody of the present invention, as described herein, in simultaneous or sequential combination with a standard of care.

Furthermore, the present invention provides an antibody of the present invention, as described herein, for use in therapy, wherein the antibody is to be administered in simultaneous or sequential combination with a standard of care. Preferably, the present invention provides an antibody of the present invention, as described herein, for use in the treatment of diabetic nephropathy, wherein the antibody is to be administered in simultaneous or sequential combination with a standard of care.

Furthermore, the present invention provides the use of an antibody of the present invention, as described herein, in the manufacture of a medicament for the treatment of diabetic nephropathy, wherein the antibody is to be administered in simultaneous or sequential combination with a standard of care.

The present invention also provides a pharmaceutical composition comprising the antigen-binding fragment of an antibody of the present invention, as described herein, and at least one pharmaceutically acceptable carrier, diluent, or excipient.

Furthermore, the present invention provides a pharmaceutical composition comprising the antigen-binding fragment of an antibody of the present invention, as described herein, together with at least one pharmaceutically acceptable carrier, diluent, or excipient, and optionally other therapeutic ingredients.

The present invention also provides a method of treating diabetic nephropathy in a patient comprising administering to the patient the antigen-binding fragment of an antibody of the present invention, as described herein.

Furthermore, the present invention provides an antigen-binding fragment of an antibody of the present invention, as described herein, for use in therapy. Preferably, the present invention provides an antigen-binding fragment of an antibody of the present invention, as described herein, for use in the treatment of diabetic nephropathy.

Furthermore, the present invention provides the use of an antigen-binding fragment of an antibody of the present invention, as described herein, in the manufacture of a medicament for the treatment of diabetic nephropathy.

The present invention also provides a method of treating diabetic nephropathy in a patient comprising administering to the patient the antigen-binding fragment of an antibody of the present invention, as described herein, in simultaneous or sequential combination with a standard of care.

Furthermore, the present invention provides an antigen-binding fragment of an antibody of the present invention, as described herein, for use in therapy, wherein the antigen-binding fragment is to be administered in simultaneous or sequential combination with a standard of care. Preferably, the present invention provides an antigen-binding fragment of an antibody of the present invention, as described herein, for use in the treatment of diabetic nephropathy, wherein the antigen-binding fragment is to be administered in simultaneous or sequential combination with a standard of care.

Furthermore, the present invention provides the use of an antigen-binding fragment of an antibody of the present invention, as described herein, in the manufacture of a medicament for the treatment of diabetic nephropathy, wherein the antigen-binding fragment is to be administered in simultaneous or sequential combination with a standard of care.

The standard of care for DN includes, but is not limited to, ACE inhibitors and angiotensin receptor blockers (ARBs).

The general structure of an "antibody" is very well-known in the art. For an antibody of the IgG type, there are four amino acid chains (two "heavy" chains and two "light" chains) that are cross-linked via intra- and inter-chain disulfide bonds. When expressed in certain biological systems, antibodies having unmodified human Fc sequences are glycosylated in the Fc region. Antibodies may be glycosylated at other positions as well. The subunit structures and three-dimensional configurations of antibodies are well known in the art. Each heavy chain is comprised of an N-terminal heavy chain variable region ("HCVR") and a heavy chain constant region ("HCCR"). The heavy chain constant region is comprised of three domains (CH1, CH2, and CH3) for IgG, IgD, and IgA; and 4 domains (CH1, CH2, CH3, and CH4) for IgM and IgE. Each light chain is comprised of a light chain variable region ("LCVR") and a light chain constant region ("LCCR").

The variable regions of each light/heavy chain pair form the antibody binding site. The HCVR and LCVR regions can be further subdivided into regions of hypervariability, termed complementarity determining regions ("CDRs"), interspersed with regions that are more conserved, termed framework regions ("FR"). Each HCVR and LCVR are composed of three CDRs and four FRs, arranged from amino-terminus to carboxy-terminus in the following order: FR1, CDR1, FR2, CDR2, FR3, CDR3, FR4. Herein, the 3 CDRs of the heavy chain are referred to as "CDRH1, CDRH2, and CDRH3" and the 3 CDRs of the light chain are referred to as "CDRL1, CDRL2 and CDRL3." The CDRs contain most of the residues which form specific interactions with the antigen. The assignment of amino acids to each domain is in accordance with well-known conventions [e.g., Kabat, "Sequences of Proteins of Immunological Interest," National Institutes of Health, Bethesda, Md. (1991)].

An antibody of the present invention may have a heavy chain constant region selected from any of the immunoglobulin classes (IgA, IgD, IgG, IgM, and IgE). Furthermore, an antibody of the present invention contains an Fc portion which is derived from human IgG4 Fc region because of its reduced ability to bind complement factors as compared to other IgG sub-types.

An antibody may be derived from a single copy or clone, including e.g., any eukaryotic, prokaryotic, or phage clone. Preferably, an antibody of the present invention exists in a homogeneous or substantially homogeneous population of antibody molecules. An full-length antibody comprises full length or substantially full length constant regions, including the Fc region. An "antigen-binding fragment" of such an antibody is any shortened form of a full length antibody that comprises the antigen-binding portion and retains antigen-binding capability. Such shortened forms include, e.g., a Fab fragment, Fab' fragment or F(ab')2 fragment that includes the CDRs or the variable regions of the antibodies disclosed. Furthermore, such shortened antibody forms can be a single chain Fv fragment that may be produced by joining the DNA encoding the LCVR and HCVR with a linker sequence. (See, Pluckthun, The Pharmacology of Monoclonal Antibodies, vol. 113, Rosenburg and Moore eds., Springer-Verlag, New York, pp 269-315, 1994). The term "antibody" does not include such fragments unless otherwise indicated. An antibody of the present invention can be produced using techniques well known in the art, e.g., recombinant technologies, phage display technologies, synthetic technologies or combinations of such technologies or other technologies readily known in the art.

An antibody of the present invention is an engineered antibody that has been designed to have frameworks, hinge regions, and constant regions of human origin that are identical with or substantially identical (substantially human) with frameworks and constant regions derived from human genomic sequences. Fully human frameworks, hinge regions, and constant regions are those human germline sequences as well as sequences with naturally-occurring somatic mutations and those with engineered mutations. An antibody of the present invention may comprise framework, hinge, or constant regions derived from a fully human framework, hinge, or constant region containing one or more amino acid substitutions, deletions, or additions therein. Further, an antibody of the present invention is substantially non-immunogenic in humans.

A variety of different human framework sequences may be used singly or in combination as a basis for an antibody of the present invention. Preferably, the framework regions of an antibody of the present invention are of human origin or substantially human (at least 95%, 97% or 99% of human origin.) The sequences of framework regions of human origin may be obtained from The Immunoglobulin Factsbook, by Marie-Paule Lafranc, Gerard Lefranc, Academic Press 2001, ISBN 012441351.

The framework sequence for an antibody of the present invention serves as the "donor" variable framework region and can be used to create additional antibodies with the same CDRs specified herein using methodology known in the art.

Furthermore, the framework sequence for an antibody of the present invention can be compared to other known human framework sequences to generate additional antibodies. Thus, this information can be used to "back-mutate" another selected homologous human framework region to the donor amino acid residue at these positions. Further, any "rare" amino acids can be detected in additional human frameworks such that the consensus or donor amino acid residue can be used at the relevant position.

"TGF-alpha" or "human TGF-alpha" refers to human TGF-alpha protein (SEQ ID NO: 18).

"Epiregulin" or "human Epiregulin" refers to human Epiregulin protein (SEQ ID NO: 33). Met-human Epiregulin (SEQ ID NO: 22) is used in in vitro experiments herein. References to the ability of the antibodies of the present invention, as described herein, to bind or to neutralize human Epiregulin pertain also to their ability to bind and to neutralize human met-Epiregulin in in vitro experiments.

A "patient" is a mammal, preferably a human.

The term "treating" (or "treat" or "treatment") means slowing, stopping, reducing, or reversing the progression or severity of a symptom, disorder, condition, or disease.

The term "therapeutically effective amount" refers to the amount or dose of an antibody of this invention which, upon single or multiple dose administration to a patient, provides the desired treatment.

The following examples may be performed essentially as described below.

EXAMPLES

Example 1

Production of Antibodies

Antibodies I and II can be made and purified as follows. An appropriate host cell, such as HEK 293 or CHO, is either transiently or stably transfected with an expression system for secreting antibodies using an optimal predetermined HC:LC vector ratio or a single vector system encoding both HC, such as SEQ ID NO: 15, and LC, such as SEQ ID NO: 16 or SEQ ID NO: 17. Clarified media, into which the antibody has been secreted, is purified using any of many commonly-used techniques. For example, the medium may be conveniently applied to a Protein A or G column that has been equilibrated with a compatible buffer, such as phosphate buffered saline (pH 7.4). The column is washed to remove nonspecific binding components. The bound antibody is eluted, for example, by pH gradient (such as 0.1 M sodium phosphate buffer pH 6.8 to 0.1 M sodium citrate buffer pH 2.5). Antibody fractions are detected, such as by SDS-PAGE, and then are pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, or hydroxyapatite chromatography. The purity of the antibody after these chromatography steps is greater than 99%. The product may be immediately frozen at −70° C. or may be lyophilized. The amino acid sequences for these antibodies are provided below.

| | SEQ ID NOs | | | |
|---|---|---|---|---|
| Antibody | Heavy Chain | Light Chain | HCVR | LCVR |
| I | 12 | 13 | 7 | 9 |
| II | 12 | 14 | 7 | 10 |
| III | 31 | 32 | 8 | 11 |

| Antibody | HCDR1 | HCDR2 | HCDR3 | LCDR1 | LCDR2 | LCDR3 |
|---|---|---|---|---|---|---|
| I | 1 | 2 | 3 | 4 | 5 | 6 |
| II | 1 | 2 | 3 | 4 | 5 | 6 |
| III | 1 | 2 | 3 | 4 | 5 | 6 |

Example 2

Affinity Binding Measurement by Surface Plasmon Reasonance (BIAcore) for Antibody I Biacore T2000 instrument (BIAcore® AB, Upsala, Sweden), reagents and Biacore T2000 Evaluation Software Ver 4.1 are used for the Surface Plasmon Resonance analysis. A CM5 chip is prepared using manufacturer's EDC/NHS amine coupling method. The surfaces of all four flow cells are activated by injecting a 1:1 mixture of EDC/NHS for 7 minutes at 10 µL/min. Goat anti-human Fc γ specific antibody is diluted to 50 µg/ml in 10 mM acetate, pH 4.0 buffer and immobilized for approximately 10000 RU onto all four flow cells by 7 minute injection at a flow rate of 10 µL/min. Un-reacted sites are blocked with a 7 minute injection of ethanolamine at 10 µL/min. Injections of 3×20 seconds of glycine pH 1.5 at 30 µL/min are used to remove non-covalently associated protein. The running buffer is HBS-EP [10 mM HEPES, 150 mM Sodium Chloride, 3 mM EDTA, 0.005% Polysorbate 20].

In study 1, Antibody I is diluted to 50 µg/mL in running buffer, and approximately 400-600 RU is captured in flowcell 2. Human TGF-alpha (SEQ ID NO: 18), rat TGF-alpha (SEQ ID NO: 20), met-human Epiregulin (SEQ ID NO: 22), and cynomolgus Epiregulin (SEQ ID NO: 24) are diluted from 100 µg/mL to 200 nM in running buffer and then two-fold serially diluted in running buffer to 6.25 nM. Mouse Epiregulin (SEQ ID NO: 23) is diluted from 100 µg/mL to 4 µM in running buffer and then two-fold serially diluted in running buffer to 125 nM. Duplicate injections of each ligand concentration are injected at 30 µL/min for 300 seconds followed by a dissociation phase. The dissociation phase is 1800 seconds for human and rat TGF-alpha, 1200 seconds for human and cynomolgus Epiregulin, and 120 seconds for mouse Epiregulin. Regeneration is performed by injecting 10 mM glycine pH 1.5 for 3×20 seconds at 30 µL/min over all flowcell.

In study 2, Antibody III is diluted to 100 mg/mL in running buffer, and approximately 400-600 RU is captured in flowcell 2. Mouse TGF-alpha (SEQ ID NO: 19), is diluted from 100 µg/mL to 200 nM in running buffer and then two-fold serially diluted in running buffer to 6.25 nM. Mouse Epiregulin (SEQ ID NO: 23) is diluted from 100 µg/mL to 4 µM in running buffer and then two-fold serially diluted in running buffer to 125 nM. Duplicate injections of each ligand concentration are injected at 30 µL/min for 300 seconds followed by a dissociation phase. The dissociation phase is 1800 seconds for mouse TGF-alpha, and 120 seconds for mouse Epiregulin. Regeneration is performed by injecting 10 mM glycine pH 1.5 for 30 seconds at 30 µL/min over all flowcell.

Reference-subtracted data are collected as Fc2–Fc1. The measurements are obtained at 25° C. The on-rate ($k_{on}$) and off-rate ($k_{off}$) for each ligand are evaluated using a "1:1 (Langmuir) Binding" binding model. The affinity ($K_D$) is calculated from the binding kinetics according to the relationship: $K_D = k_{off}/k_{on}$.

TABLE 1

Binding Parameters for Antibody I

| Ligand | Species | On Rate ($k_{on}$) ($M^{-1}s^{-1}$) (±SD) | Off Rate ($k_{off}$) ($s^{-1}$) (±SD) | Affinity ($K_D{}^a$) (±SD) |
|---|---|---|---|---|
| TGF-alpha | Human | $4.18 \pm 0.28 \times 10^5$ | $4.09 \pm 0.96 \times 10^{-5}$ | $97.6 \pm 20.6$ pM |
|  | Rat | $3.78 \pm 0.39 \times 10^5$ | $2.66 \pm 0.74 \times 10^{-5}$ | $70.5 \pm 19.4$ pM |
| Epiregulin | Human | $4.91 \pm 0.42 \times 10^5$ | $6.31 \pm 0.55 \times 10^{-4}$ | $1.29 \pm 0.03$ nM |
|  | Cynomolgus | $6.73 \pm 0.71 \times 10^5$ | $7.05 \pm 0.23 \times 10^{-4}$ | $1.05 \pm 0.09$ nM |
|  | Mouse | $4.10 \pm 1.15 \times 10^4$ | $1.33 \pm 0.16 \times 10^{-2}$ | $342 \pm 136$ nM |

$^a$Calculated as $K_D = k_{off}/k_{on}$

TABLE 2

Binding Parameters for Antibody III

| Ligand | On Rate ($k_{on}$) ($M^{-1}s^{-1}$) (±SD) | Off Rate ($k_{off}$) ($s^{-1}$) (±SD) | Affinity ($K_D{}^a$) (±SD) |
|---|---|---|---|
| Mouse TGF-alpha | $5.41 \pm 0.50 \times 10^5$ | $2.02 \pm 0.54 \times 10^{-5}$ | $38.0 \pm 13.6$ pM |
| Mouse Epiregulin | $6.55 \pm 0.38 \times 10^4$ | $1.41 \pm 0.09 \times 10^{-2}$ | $215 \pm 15$ nM |

$^a$Calculated as $K_D = k_{off}/k_{on}$

Antibody I binds to human TGF-alpha and human Epiregulin with affinities of about 98 pM and 1.3 nM, respectively. Antibody I also binds to rat TGF-alpha and mouse Epiregulin with affinities of about 70 pM and 340 nM, respectively. Additionally, Antibody I binds to cynomolgus Epiregulin with an affinity of about 1 nM. Antibody III binds to mouse TGF-alpha and mouse Epiregulin with affinities of about 38 pM and 220 nM, respectively. Thus, Antibody I and Antibody III of the present invention have high affinity to human TGF-alpha and human Epiregulin.

Example 3

Internalization of EGF Target Ligands in the Human Colon Carcinoma Cell Line HT-29

Conjugation of Alexa Fluor® 488 to Antibodies

Alexa Fluor® 488 is conjugated to Antibody I and Control IgG according to the manufacturer's protocol. Protein is diluted to 2 mg/mL in PBS. To 0.5 mL of this 2 mg/mL solution, 50 µL of 1M sodium bicarbonate pH 9 is added. The protein solution is then transferred to a vial of dye and stirred at room temperature for 1 hour. The labeled protein is purified using the Bio-Rad BioGel P-30 resin included with the labeling kit.

In Vitro Internalization Assay

In study 1, 10,000 HT-29 cells, a colon adenocarcinoma cell line known to express TGF-alpha and Epiregulin, are seeded per well of a 96 well plate and allowed to incubate overnight in complete media [Dulbecco's Modified Eagle's Medium/F12 (Ham) Medium (1:1) ("DMEM/F12") containing L-glutamine, 10% heat-inactivated fetal bovine serum ("FBS"), 1× antibiotic, and 2.438 g/L sodium bicarbonate]. The next day, the cells are washed with PBS containing 0.1% BSA and then incubated with an Alexa Fluor® 488 conjugated Antibody I or Control IgG in PBS with 0.1% BSA at concentrations ranging from 0 to 88 ug/mL for 2 hours at 37° C. in a tissue culture incubator. Following the incubation period, the cells are washed in PBS with 0.1% BSA several times and then fixed with 4% formaldehyde for analysis. The quantitation of internalization is done as follows: 500 cells/well are collected with a Cellomics Arrayscan VTI (Thermo Scientific). Image analysis is performed with "Compartmental analysis" Bioapplications of the system. Cell nuclei are identified with a Hoechst stain (blue). Two regions of interest (ROI) are set to collect fluorescent signals from intracellular spots (red) and total green fluorescence (both red and blue) obtained from the masked image. The number, area and fluorescent intensity from each spot and cell are calculated. The mean spot total intensity of intracellular spots (red) is chosen for measuring Antibody I induced internalization.

In study 2, 10,000 HT-29 cells are prepared as previously described, and Alexa Fluor® 488 conjugated Antibody I or Control IgG in PBS containing 0.1% BSA is added to the cells at 40 ug/mL. Cells are incubated at 37° C. in a tissue culture incubator for various times ranging from 0-120 minutes, then washed with PBS containing 0.1% BSA several times and fixed with 4% formaldehyde for analysis. The quantification of signal is performed essentially as previously described.

TABLE 3a

Study 1 - Mean Ringspot Total Intensity of Fluorescence

| Dose (ug/ml) | 88 | 44 | 22 | 11 | 5.5 |
|---|---|---|---|---|---|
| Control IgG | 2440 ± 199 | 1808 ± 207 | 1763 ± 68 | 1391 ± 76 | 1357 ± 63 |
| Antibody I | 24809 ± 4343 | 17451 ± 217 | 15135 ± 131 | 11516 ± 54 | 8474 ± 269 |

Mean ± SEM

TABLE 3b

Study 1 - Mean Ringspot Total Intensity of Fluorescence

| Dose (ug/ml) | 2.75 | 1.38 | 0.69 | 0.34 | 0 |
|---|---|---|---|---|---|
| Control IgG | 1570 ± 70 | 1473 ± 7 | 1483 ± 90 | 1407 ± 41 | 1630 ± 155 |
| Antibody I | 6503 ± 262 | 4349 ± 186 | 3440 ± 96 | 2432 ± 62 | 1460 ± 84 |

Mean ± SEM

The results from the imaging analysis of study 1 determined that the fluorescence signal was internalized into the cell and was dose dependent with Antibody I, but not with the Control IgG (Table 3a and Table 3b).

TABLE 4

Study 2 - Mean Ringspot Total Intensity of Fluorescence

| | Time post addition (min) | | | | | |
|---|---|---|---|---|---|---|
| | 120 | 60 | 30 | 15 | 5 | 0 |
| Control IgG | 177 ± 29 | 167 ± 23 | 124 ± 10 | 126 ± 18 | 116 ± 4 | 94 ± 11 |
| Antibody I | 4449 ± 866 | 4131 ± 1688 | 1494 ± 66 | 717 ± 72 | 261 ± 17 | 89 ± 1 |

Mean ± SEM

The results from study 2 demonstrated that Antibody I was internalized rapidly and the internalization was complete by 2 hours post addition to cells (Table 4). Antibody I induced internalization of target on HT-29 cells in vitro in a time dependent manner (Table 4).

Example 4

Measurement of Neutralization of EGFR Ligand Stimulated Cell Proliferation in a Myofibroblast Cell Line A clonal mouse myofibroblast cell line ("MFc7") is used to test the ability of the antibodies of the present invention to block the proliferative activity of EGFR ligands. The seven ligands that can activate the EGFR are TGF-alpha (TGFA), Epiregulin (EREG), EGF, Heparin-Binding EGF (HB-EGF), Epigen (EPGN), Amphiregulin (AREG) and Betacellulin (BTC). The EGFR ligands share a structural motif, the EGF-like domain, characterized by three intramolecular disulfide bonds that are formed by six similarly spaced conserved cysteine residues. Proliferative activity is determined by Bromodeoxyuridine ("BrDU") incorporation and is measured with a colorimetric BrDU ELISA kit according to the manufacturer's instructions.

First, 2,000 MFc7 cells/well are plated in a tissue culture treated 96 well microplate in 0.1 mL of Dulbecco's Modified Eagle's Medium/F12 (Ham) Medium (1:1) ("DMEM/F12") containing L-glutamine, 10% heat-inactivated FBS, 1× antibiotic, and 2.438 g/L sodium bicarbonate. Cells are allowed to attach for 6 hours, and then the medium is removed and replaced with 0.1 mL of serum free DMEM/F12 containing 0.1% BSA for serum starvation overnight. The next day, serial dilutions of the EGFR ligands are made with serum free media containing 0.1% BSA in 96 well polypropylene plates in a volume of 0.12 mL/well from concentrations ranging from 0.001 to 3000 ng/mL. Following dilutions, medium is removed from serum starved cells and then stimulated with EGFR ligand for 24 hrs. Following stimulation, the cells are pulsed with BrDU for 4 hrs and then analyzed with a colorimetric BrDU ELISA kit according to the manufacturer's instructions.

In testing the specificity of Antibody I to EGFR ligands, serial dilutions of 2× or 3× of the antibody are made in 96 well polypropylene plates in a volume of 0.06 mL/well from concentrations ranging from 3000 nM to 0.059 nM. Following serial dilutions of the antibody, 0.06 mL of the EGFR ligand is added per well. The plate is then incubated at 37° C. in a humidified tissue culture incubator for 30 minutes. Following incubation, 0.1 mL of the solution is transferred per well to the cells. The cells are stimulated for 24 hours. Following stimulation, the cells are pulsed with BrDU for 4 hours and then analyzed with a colorimetric BrDU ELISA kit. Absorbance values (450 nM-690 nM) are generated on a SpectraMax 190 plate reader (Molecular Devices) and data are analyzed.

TABLE 5

| | MFc7 Assay | | |
|---|---|---|---|
| EGFR Ligand | EC50 Range (pM) | IC50 (nM) Antibody I | IC50 (nM) Antibody III |
| Human TGF-alpha[a] | 11-12 | 0.46 ± 0.03 | 0.52 ± 0.04 |
| Human Epiregulin | 78-282 | 3.15 ± 1.04 | 1.12 ± 0.36 |
| Human Epigen | 3797-18987 | 807 ± 577 | nd[b] |
| Human EGF | 0.3-2.4 | >2000 | nd[b] |
| Human HBEGF | 30-39 | >2000 | nd[b] |
| Human Betacellulin | 1.8-3.2 | >2000 | nd[b] |
| Human Amphiregulin | 273-2727 | >2000 | nd[b] |
| Rat TGF-alpha | 13-13.8 | 0.19 ± 0.06 | 0.13 ± 0.01 |
| Mouse Epiregulin | 163-320 | 334 ± 41 | 214 ± 49 |

[a]Human EGFR ligands were at a concentration of 0.5 nM when tested with Antibody I, except for Amphiregulin (60 nM) and Epigen (100 nM)
Rat TGF-alpha and Mouse Epiregulin were used at 0.5 nM
[b]nd, not determined Mouse Epiregulin and rat TGF-alpha, as well as all of the human EGFR ligands except for Epigen and Amphiregulin were found to be potent stimulators of cell proliferation in the assay (Table 5). Antibody I and Antibody III have high affinity to human and rat TGF-alpha and human Epiregulin activity (Table 5).

Table 5 summarizes the calculated EC50 values for the EGFR ligands tested and the absolute IC50 values for the antibodies to those ligands. The calculated average IC50 for Antibody I was 0.46±0.03 nM to human TGF-alpha and 3.15±1.04 nM to human Epiregulin. The calculated IC50 average for Antibody III was 0.52±0.04 nM to human TGF-alpha and 1.12±0.36 nM to human Epiregulin. The calculated average IC50 value for Antibody III was 0.13±0.01 nM to rat TGF-alpha and 214±49 nM to mouse Epiregulin. Thus, Antibody I and Antibody III have high affinity and are selective with full neutralizing activity against human TGF-alpha and human Epiregulin.

Example 5

Renal Function and Pathology in a Mouse Remnant Kidney Model of Hypertensive Renal Disease A mouse remnant kidney model involving surgical reduction of 75% of the total renal mass is used as a preclinical model of hypertensive renal disease. [Ma L J, Fogo A B. Kidney Int. 2003 July; 64(1):350-5] Surgical reduction of renal mass or sham surgery is done in male 129 Svev mice at 9-10 weeks of age. Randomization into groups of 12 mice is done at 2 weeks post surgery, by urine albumin/creatinine ratio ("ACR") and body weight. An isotype Control IgG (10 mg/kg) or Antibody III (1 and 10 mg/kg) are dosed subcutaneously following randomization and continued once weekly out to week 16 post surgery. The endpoints for the study are survival, systolic blood pressure, albuminuria, serum creatinine, serum BUN, urine TGF-alpha, urine MIP-2 and renal pathology.

At the end of the study, there were 3 deaths in the Control IgG group (25% mortality) with no deaths in the Antibody III treatment groups.

Measurement of Systolic Blood Pressure

Blood pressure is taken at 12 weeks post surgery by the tail cuff method. Selected mice from each group (N=3-4 per group) are acclimated to the restraint by placing them in the mouse holder with the tail cuff attached for 5 minutes daily, 3-5 days prior to the actual measurement. The equipment room temperature is increased to 24° C. to provide additional warmth during the blood pressure collection process. The mice are placed in a mouse restrainer and set on top of a warming pad unit (31-33° C.) to provide dilation to the tail vasculature. The tail is placed through the tail cuff and each mouse is restrained for an approximate time of 30 minutes, not to exceed 45 minutes. This time includes the initial warming and pressure measurements followed by immediate return to general housing. No anesthesia is used. The tail cuff is inflated, compressing the tail tightly enough to momentarily interrupt arterial blood flow, and then is gradually loosened by deflation to observe the return of the arterial pulse. On return of arterial pulse, the cuff is fully deflated.

Measurement of Albuminuria

Urine is collected every 4 weeks in Nalgene Metabolic cage units over a 24 hour time period. Each mouse (singly housed) receives food and water during the 24 hour collection process. At the end of the 24 hour period, the collected urine is placed on ice, centrifuged and subjected to albumin and creatinine analysis. Albuminuria is defined as the ratio of urine albumin to creatinine (ug/mg).

Serum Creatinine and BUN

At study termination, serum obtained by cardiac puncture is analyzed for BUN and creatinine.

TGF-Alpha and MIP-2 ELISA

Urine obtained by a 24 hour collection is concentrated 5-fold centrifugally using a 3K MW cutoff membrane spun at 14,000×g for 30 minutes. A sandwich-type enzyme-linked immunosorbent assay ("ELISA") for mouse TGF alpha is established. Rat TGF-alpha is used as the standard. Polystyrene 96-well plates are coated with 3 µg/mL of Antibody III overnight at 4° C. Plates are washed, blocked with blocking buffer, washed again, and then the concentrated urine samples are added. After 2 hours at room temperature, plates are washed, and then secondary biotinylated polyclonal anti-hTGF alpha is added. After 2 hours at room temperature, plates are washed and incubated with streptavidin-HRP for 30 minutes. Signal is generated with TMB substrate, and the reaction is stopped with 2 N H2SO4. A commercial Quantikine® sandwich ELISA kit for mouse macrophage inflammatory protein 2 (MIP-2, the equivalent of human IL-8) is used to detect urine MIP-2 according to the manufacturer's instructions. Absorbance data for both ELISA assays are obtained on a SpectraMax 190 plate reader (Molecular Devices) and data are analyzed.

Renal Pathology

Remnant kidneys are removed at study termination, fixed in formalin and processed for paraffin sectioning according to standard methodology. Sections of kidney are evaluated for renal lesions by a pathologist. Tubular protein, increased mesangial matrix and interstitial fibrosis, are semi-quantitatively scored using the following scale: none (0), minimal (1), slight (2), moderate (3), marked (4) and severe (5). Glomerular mesangial matrix expansion and basement membrane thickening are scored using hematoxylin and eosin ("H&E") and Periodic acid-Schiff ("PAS") stained sections. Masson's trichrome stained sections of kidney are evaluated to determine the degree of fibrosis (interstitial and glomerular).

Statistical Methods

All data are analyzed with JMP v.8.0 software (SAS Institute). Pathology scores are statistically evaluated by a contingency analysis and a Fishers exact test. All other data are evaluated by ANOVA with log transformed data and a Students unpaired t test. A P value of <0.05 is considered statistically significant.

TABLE 6

Albuminuria progression over time

| Weeks | 2 | 4 | 8 | 12 | 16 |
|---|---|---|---|---|---|
| Control IgG (10 mg/kg) | 1601 ± 269 | 3377 ± 860 | 5201 ± 907 | 6144 ± 1654 | 4863 ± 2170 |
| Antibody III (1 mg/kg) | 1665 ± 305 | 3211 ± 343 | 3224 ± 518 | 3790 ± 857 | 5240 ± 2004 |
| Antibody III (10 mg/kg) | 1626 ± 273 | 2245 ± 334 | 2399 ± 261[a] | 2749 ± 401[a] | 3254 ± 654 |

Arithmetic mean ± SEM for the urine albumin to creatinine ratio (ug/mg)
[a]Statistically significant difference compared to the Control IgG (p < 0.05)

There was a dose dependent decrease in albuminuria relative to the Control IgG group with Antibody III (Table 6). Antibody III treatment at 10 mg/kg resulted in a significant reduction in albuminuria at weeks 8 and 12 post surgery relative to the Control IgG group, but not at weeks 2, 4, or 16 (Table 6).

TABLE 7

Systolic blood pressure, Serum Creatinine and BUN

| Endpoint | Week 12 Systolic Blood Pressure (mm Hg) | Week 16 Serum Creatinine (mg/dL) | Week 16 Serum BUN (mg/dL) |
|---|---|---|---|
| Sham | nd | 0.17 ± 0.01 | 31.5 ± 2.5 |
| Control IgG (10 mg/kg) | 139.6 ± 4.0 | 0.31 ± 0.04[a] | 64.0 ± 12.5[a] |
| Antibody III (1 mg/kg) | 147.5 ± 8.2 | 0.29 ± 0.01[a] | 47.6 ± 1.7 |
| Antibody III (10 mg/kg) | 157.3 ± 4.5 | 0.23 ± 0.01[b] | 44.8 ± 1.5[b] |

Arithmetic mean ± SEM
[a]Statistically significant relative to the sham group (p < 0.05)
[b]Statistically significant difference compared to the Control IgG group (p < 0.05)
nd, not determined Antibody III demonstrated no effect on the systolic blood pressure, as all groups demonstrated hypertension at 12 weeks post surgery (Table 7). Furthermore, Antibody III treatment at 10 mg/kg resulted in improvements in renal function as shown by significant reductions in serum creatinine and BUN relative to the Control IgG group (Table 7).

TABLE 8

Urine TGF-alpha, Urine MIP-2 and renal pathology scores

| Endpoint | Week 8 Urine TGF-alpha to Creatinine (pg/mg) | Week 12 Urine MIP-2 to Creatinine (pg/mg) | Week 16 Pathology Tubular Protein Score (1-5) | Week 16 Pathology Mesangial Matrix Score (1-5) | Week 16 Pathology Interstitial Fibrosis Score (1-5) |
|---|---|---|---|---|---|
| Sham | 115 ± 4 | Not detectable | 0 ± 0 | 0 ± 0 | 0.25 ± 0.25 |
| Control IgG (10 mg/kg) | 102 ± 53 | 22.8 ± 7.4 | 2.55 ± 0.16 | 1.91 ± 0.28 | 2.09 ± 0.16 |
| Antibody III (1 mg/kg) | 74 ± 18 | nd | 2.17 ± 0.11 | 1.58 ± 0.15 | 1.83 ± 0.21 |
| Antibody III (10 mg/kg) | 19 ± 5$^a$ | 5.6 ± 0.9$^a$ | 2.08 ± 0.08$^a$ | **1.42 ± 0.15 | 1.42 ± 0.15$^a$ |

Arithmetic mean ± SEM
$^a$Statistically significant difference compared to the Control IgG group (p < 0.05)
nd, not determined There was a statistically significant reduction in urine TGF-alpha and urine MIP-2 at weeks 8 and 12 post surgery respectably with the 10 mg/kg Antibody III dose compared to the Control IgG group (Table 8). Furthermore, there were statistically significant reductions in renal pathology for tubular protein and interstitial fibrosis and a decrease in mesangial matrix expansion with the 10 mg/kg dose of Antibody III compared to the Control IgG (Table 8).

Example 6

Albuminuria and Renal Pathology in a Mouse Uninephrectomy db/db Model of Diabetic Renal Disease The uninephrectomized db/db mouse model represents a model of diabetic nephropathy. [Ninichuk et al., Eur J Med Res. 2007 Aug. 16; 12(8):351-5] The uninephrectomized db/db model is used to determine the effects of Antibody III on renal disease parameters due to diabetes. The uninephrectomy ("UniNx") surgery on db/db mice on a C57BLKS/J background is performed at 4 weeks of age with removal of the right kidney. Randomization into groups of 12 mice is done at 8 weeks of age, by urine ACR, blood glucose and body weight. All the mice are hyperglycemic at the beginning of each study. An isotype Control IgG or Antibody III are dosed subcutaneously starting at 9 weeks of age and continued once weekly out to 25 weeks of age. Study 1 is conducted with doses of 0.3 and 10 mg/kg of Antibody III and a 10 mg/kg dose of isotype Control IgG. The endpoints for study 1 are survival, % HbA1c, albuminuria, urine TGF-alpha, kidney weight and renal pathology. Study 2 contains dose groups of 30, 10, 3 and 0.3 mg/kg of Antibody III with a 30 mg/kg dose of an isotype Control IgG. The endpoints for study 2 are survival and albuminuria.

There was only one death in the Control IgG group in study 1. There were no deaths in study 2.

Urine Collection and Measurement of Albuminuria

Urine is collected by a spot collection method to collect urine over a 2-4 hour time period. An individual mouse is placed on top of a 96 well polypropylene microplate and then covered by a Plexiglas chamber with holes for breathing but no access to food or water. At the end of the time period, the urine is removed from the plate with a micropipette and placed on ice, centrifuged and subjected to albumin and creatinine analysis. Albuminuria is defined as the ratio of urine albumin to creatinine (ug/mg).

Determination of % HbA1c

The % HbA1c is used as a measure of hyperglycemia at the end of the study. EDTA plasma is obtained at necropsy by cardiac puncture. Blood samples are spun at 2000 g for 20 minutes to remove blood cells and obtain plasma. Plasma samples are analyzed for Hemoglobin A1c and Total Hemoglobin. From these data, the % HbA1c as calculated.

Kidney Weight

Kidneys are removed at necropsy to determine their weight.

Determination of Urine TGF-Alpha by ELISA

Urine obtained by a spot collection is concentrated 5-fold with a 0.5 mL Amicon Ultra centrifugal filter containing an ultracel 3K MW cutoff membrane. The device is spun at 14,000×g for 30 minutes, and then the concentrated urine samples are collected. A sandwich-type ELISA for mouse TGF alpha is established. Rat TGF-alpha is used as the standard for the TGF-alpha ELISA. Polystyrene 96-well plates are coated with 3 μg/mL of Antibody III overnight at 4° C. Plates are washed, blocked with blocking buffer, washed again, and then the concentrated urine samples are added. After 2 hours at room temperature, plates are washed, and then secondary biotinylated polyclonal anti-hTGF-alpha is added. After 2 hours at room temperature, plates are washed and incubated with streptavidin-HRP for 30 minutes. Signal is generated with TMB substrate, and the reaction is stopped with 2 N H2SO4. Absorbance data are obtained on a SpectraMax 190 plate reader (Molecular Devices) and data are imported into Microsoft Excel 2007 and Sigmaplot v.9.01 for analysis.

Renal Pathology

Kidneys are removed at study termination, capsules removed and then fixed in formalin and processed for paraffin sectioning according to standard methodology. Sections of kidney are evaluated for renal lesions by a pathologist. Mesangial matrix, pelvic dilation and glomerular fibrosis, are semi-quantitatively scored using the following scale: none (0), minimal (1), slight (2), moderate (3), marked (4) and severe (5). Glomerular mesangial matrix expansion and basement membrane thickening are scored using H&E and PAS stained sections. Masson's trichrome stained sections of kidney are evaluated to determine the degree of fibrosis (glomerular).

Statistical Methods

All data are analyzed with JMP v.8.0 software (SAS Institute). Pathology scores are statistically evaluated by a contingency analysis and a Fishers exact test. Statistical analysis of albuminuria (ACR) is done by a Fit model with nontransformed data and the baseline ACR at week 8 as a covariate. ACR progression is analyzed by comparing the week 24 data with the week 16 data within each group by ANOVA and a Student's unpaired t test. The ACR change from week 16 to week 24 across groups is done by ANOVA and a student's unpaired t test. A P value of <0.05 is considered statistically significant. All other data are evaluated by ANOVA with log transformed data and a Students unpaired t test.

TABLE 9

Study 1 - Albuminuria progression

| | Age (Weeks) | | | | | Wk 16-24 ACR change (ug/mg) | Wk 16-24 ACR change (%) |
|---|---|---|---|---|---|---|---|
| | 8 | 12 | 16 | 20 | 24 | | |
| Healthy Lean | nd | 15 ± 2 | 19 ± 3 | 13 ± 3 | 12 ± 2 | nd | nd |
| Db/db Control IgG @ 10 mg/kg | 273 ± 59$^a$ | 903 ± 125$^a$ | 1551 ± 180$^a$ | 2384 ± 257$^a$ | 3228 ± 488$^{ac}$ | 1677 ± 419 | 108 ± 27 |
| Db/db Antibody III @ 0.3 mg/kg | 299 ± 63$^a$ | 913 ± 174$^a$ | 1573 ± 209$^a$ | 1911 ± 222$^a$ | 2248 ± 417$^{ab}$ | 675 ± 332$^b$ | 43 ± 21 |
| Db/db Antibody III @ 10 mg/kg | 291 ± 55$^a$ | 1002 ± 107$^a$ | 965 ± 141$^a$ | 1433 ± 190$^{ab}$ | 1426 ± 230$^{ab}$ | 461 ± 219$^b$ | 48 ± 23 |

Arithmetic mean ± SEM
$^a$Statistically significant relative to the healthy lean group (p < 0.05)
$^b$Statistically significant difference compared to the Control IgG group (p < 0.05)
$^c$Statistically significant relative to the week 16 timepoint within that group (p < 0.05)

In Study 1, there was a dose dependent decrease in albuminuria relative to the Control IgG group with Antibody III (Table 9). There was less progression of albuminuria compared to the Control IgG group for both the Antibody III groups during the last two months. The change in albuminuria within the group over the last two months of the study indicated that the Control IgG group significantly increased from week 16 to week 24, while the Antibody III groups did not (Table 9). In Study 2, there was a dose dependent reduction in the albuminuria progression over time with Antibody III compared to the Control IgG (Table 9).

TABLE 10

Study 2 - Albuminuria progression

| | Age (Weeks) | | | | | Wk 16-24 ACR change (ug/mg) | Wk 16-24 ACR change (%) |
|---|---|---|---|---|---|---|---|
| | 8 | 12 | 16 | 20 | 24 | | |
| Healthy Lean | nd | 13 ± 0 | 15 ± 0 | 9 ± 0 | 9 ± 0 | nd | nd |
| Db/db Control IgG @ 30 mg/kg | 358 ± 76$^a$ | 1325 ± 271$^a$ | 1621 ± 350$^a$ | 2219 ± 320$^a$ | 2397 ± 242$^a$ | 776 ± 379 | 48 ± 23 |
| Db/db Antibody III @ 0.3 mg/kg | 356 ± 60$^a$ | 1200 ± 213$^a$ | 2410 ± 393$^a$ | 2286 ± 416$^a$ | 2086 ± 394$^a$ | −323 ± 279$^b$ | −13 ± 12$^b$ |
| Db/db Antibody III @ 3 mg/kg | 367 ± 77$^a$ | 1122 ± 248$^a$ | 1670 ± 193$^a$ | 1427 ± 204$^a$ | 1544 ± 264$^{ab}$ | −126 ± 208$^b$ | −8 ± 12$^b$ |
| Db/db Antibody III @ 10 mg/kg | 326 ± 77$^a$ | 1107 ± 304$^a$ | 1659 ± 286$^a$ | 1202 ± 189$^{ab}$ | 1171 ± 252$^{ab}$ | −489 ± 275$^b$ | −29 ± 17$^b$ |
| Db/db Antibody III @ 30 mg/kg | 308 ± 68$^a$ | 1155 ± 179$^a$ | 1669 ± 223$^a$ | 1334 ± 237$^a$ | 950 ± 132$^{ac}$ | −719 ± 230$^b$ | −43 ± 14$^b$ |

Arithmetic mean ± SEM
$^a$Statistically significant difference relative to the healthy lean group (p < 0.05)
$^b$Statistically significant difference compared to the Control IgG group (p < 0.05)
$^c$Statistically significant relative to the week 16 timepoint within a group (p < 0.05)

The change in albuminuria over the last two months of Study 2 indicated that 30 mg/kg Antibody III resulted in a significant reduction of albuminuria over the last two months of the study, while the Control IgG increased over the same time period (Table 10).

TABLE 11

HbA1c, Kidney weight, urine TGF alpha and renal pathology scores

| Endpoint | HbA1c (%) | Kidney weight (mgs) | Wk8 Urine TGF alpha (pg/mg) | Wk24 Urine TGF alpha (pg/mg) | Pathology Mesangial Matrix Score (1-5) | Pathology Pelvic Dilation Score (1-5) |
|---|---|---|---|---|---|---|
| Healthy Lean | 4.1 ± 0.0 | 138 ± 4 | nd | nd | 0 ± 0 | 0 ± 0 |
| Db/db Control IgG @ 10 mg/kg | 11.1 ± 0.3$^a$ | 396 ± 13$^a$ | 215 ± 17 | 199 ± 18 | 1.92 ± 0.08$^a$ | 1.67 ± 0.14$^a$ |
| Db/db Antibody III @ 0.3 mg/kg | 11.2 ± 0.4$^a$ | 375 ± 14$^a$ | 208 ± 17 | 145 ± 30$^b$ | 1.64 ± 0.15$^a$ | 0.45 ± 0.16$^{ab}$ |
| Db/db Antibody III @ 10 mg/kg | 10.7 ± 0.4$^a$ | 359 ± 12$^{ab}$ | 193 ± 16 | 3 ± 1$^b$ | 1.17 ± 0.11$^{ab}$ | 0.25 ± 0.13$^{ab}$ |

Arithmetic mean ± SEM
$^a$Statistically significant difference relative to the healthy lean group ($p < 0.05$)
$^b$Statistically significant difference compared to the Control IgG group ($p < 0.05$)

Left Kidney weight was significantly lower in the 10 mg/kg Antibody III group relative to the 10 mg/kg Control IgG and 0.3 mg/kg Antibody III groups (Table 11). There was a significant decrease in urine TGF-alpha over the course of the study in the Antibody III 10 mg/kg dose group (Table 11). Furthermore, the % HbA1c for all the treatment groups were significantly elevated over the Control lean mice (Table 11). Antibody III treatment did not affect the % HbA1c compared to the Control IgG group (Table 11). Furthermore, there were significant reductions in renal pathology scores for mesangial matrix expansion and pelvic dilation with 10 mg/kg of Antibody III compared to the Control IgG (Table 11).

Example 7

Toxicity and Toxicokinetic Study in Cynomolgus Monkeys Given Weekly Intravenous Bolus Injections for 6 Weeks A 6-week toxicology study is conducted in monkeys to evaluate whether inhibition of TGF-alpha and Epiregulin would lead to skin toxicity. Monkeys are dosed with vehicle, 10 or 100 mg/kg of Antibody I intravenous injection (IV) on a weekly basis for 6 weeks. The injection site is alternated between the right and left saphenous veins. Feed is provided twice daily (once in the morning and once in the afternoon). The morning food ration is provided soon after dosing on dosing days. Supplements and treats high in calcium are not offered during the study. A children's multivitamin is offered once weekly on Saturdays (after the 96-hour post-dose blood collections, where applicable).

Monkeys are housed in "divided pair" stainless steel slat/mesh cages throughout the study. During the first three weeks, the animals are individually housed. For the remainder of the study, the animals are pair-housed within treatment groups, beginning each afternoon and continuing until the following morning, in order to provide additional opportunity for socialization.

The No-Observed-Adverse-Effect Level ("NOAEL") for this study was 100 mg/kg of Antibody I. No skin changes were observed in treated animals. There were no other pathology changes observed.

We claim:

1. An antibody that binds TGF-alpha and Epiregulin, comprising a light chain and a heavy chain, wherein the light chain comprises a light chain variable region (LCVR) and the heavy chain comprises a heavy chain variable region (HCVR), wherein the LCVR comprises amino acid sequences LCDR1, LCDR2, and LCDR3, and the HCVR comprises amino acid sequences HCDR1, HCDR2, and HCDR3, wherein LCDR1 is SEQ ID NO:4, LCDR2 is SEQ ID NO:5, LCDR3 is SEQ ID NO:6, HCDR1 is SEQ ID NO:1, HCDR2 is SEQ ID NO:2, and HCDR3 is SEQ ID NO:3.

2. The antibody of claim 1, wherein the amino acid sequence of the LCVR is SEQ ID NO:9 or SEQ ID NO:10.

3. The antibody of claim 1, wherein the amino acid sequence of the HCVR is SEQ ID NO:7.

4. The antibody of claim 1, wherein the amino acid sequence of the LCVR is SEQ ID NO:9 and the amino acid sequence of the HCVR is SEQ ID NO:7.

5. The antibody of claim 2, wherein the amino acid sequence of the light chain is SEQ ID NO:13 or SEQ ID NO:14.

6. The antibody of claim 3, wherein the amino acid sequence of the heavy chain is SEQ ID NO:12.

7. An antibody that binds TGF-alpha and Epiregulin, comprising two light chains wherein the amino acid sequence of each light chain is SEQ ID NO:13, and two heavy chains wherein the amino acid sequence of each heavy chain is SEQ ID NO:12.

8. An antibody that binds TGF-alpha and Epiregulin, comprising two light chains wherein the amino acid sequence of each light chain is SEQ ID NO:14, and two heavy chains wherein the amino acid sequence of each heavy chain is SEQ ID NO:12.

9. A pharmaceutical composition comprising the antibody of claim 1, and at least one pharmaceutically acceptable carrier, diluent, or excipient.

10. A method of treating diabetic nephropathy in a patient, comprising administering to the patient a therapeutically effective amount of the antibody of claim 1.

11. A pharmaceutical composition comprising the antibody of claim 7, and at least one pharmaceutically acceptable carrier, diluent, or excipient.

12. A method of treating diabetic nephropathy in a patient, comprising administering to the patient a therapeutically effective amount of the antibody of claim 7.

13. A pharmaceutical composition comprising the antibody of claim 8, and at least one pharmaceutically acceptable carrier, diluent, or excipient.

14. A method of treating diabetic nephropathy in a patient, comprising administering to the patient a therapeutically effective amount of the antibody of claim 8.

* * * * *

SEQUENCE LISTING

<160> NUMBER OF SEQ ID NOS: 33

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Tyr Thr Phe Thr Asp Ala Tyr Ile Asn
1               5                   10

<210> SEQ ID NO 2
<211> LENGTH: 17

```
<212> TYPE: PRT
<213> ORGANISM: Artificial Sequence
<220> FEATURE:
<223> OTHER INFORMATION: Synthetic Construct

<400> SEQUENCE: 2

Trp Ile Trp Pro Gly Pro Val Ile Thr Tyr Tyr Asn Pro Lys Phe Lys
1               5                   10                  15

Gly

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Arg Glu Val Leu Ser Pro Phe Ala Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

Arg Ser Ser Gln Ser Ile Val His Ser Thr Gly Asn Thr Tyr Leu Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Phe His Gly Thr His Val Pro Tyr Thr
1               5

<210> SEQ ID NO 7
<211> LENGTH: 118
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Ala
                20                  25                  30
```

```
Tyr Ile Asn Trp Val Arg Gln Ala Pro Gly Gln Gly Leu Glu Trp Met
        35                  40                  45

Gly Trp Ile Trp Pro Gly Pro Val Ile Thr Tyr Tyr Asn Pro Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Glu Val Leu Ser Pro Phe Ala Tyr Trp Gly Gln Gly Thr
                100                 105                 110

Thr Val Thr Val Ser Ser
        115
```

<210> SEQ ID NO 8
<211> LENGTH: 118
<212> TYPE: PRT
<213> ORGANISM: Artificial Sequence
<220> FEATURE:
<223> OTHER INFORMATION: Synthetic Construct

<400> SEQUENCE: 8

```
Gln Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Thr Asp Ala
                 20                  25                  30

Tyr Ile Asn Trp Val Lys Gln Arg Pro Gly Gln Gly Leu Glu Trp Ile
        35                  40                  45

Gly Trp Ile Trp Pro Gly Pro Val Ile Thr Tyr Tyr Asn Pro Lys Phe
 50                  55                  60

Lys Gly Lys Ala Thr Leu Thr Val Asp Lys Ser Ser Ser Thr Ala Tyr
 65                  70                  75                  80

Met Leu Leu Ser Ser Leu Thr Ser Glu Asp Ser Ala Phe Tyr Phe Cys
                 85                  90                  95

Ala Arg Arg Glu Val Leu Ser Pro Phe Ala Tyr Trp Gly Gln Gly Thr
                100                 105                 110

Leu Val Thr Val Ser Ala
        115
```

<210> SEQ ID NO 9
<211> LENGTH: 112
<212> TYPE: PRT
<213> ORGANISM: Artificial Sequence
<220> FEATURE:
<223> OTHER INFORMATION: Synthetic Construct

<400> SEQUENCE: 9

```
Asp Ile Val Met Thr Gln Ser Pro Asp Ser Leu Ala Val Ser Leu Gly
 1               5                  10                  15

Glu Arg Ala Thr Ile Asn Cys Arg Ser Ser Gln Ser Ile Val His Ser
                 20                  25                  30

Thr Gly Asn Thr Tyr Leu Glu Trp Tyr Gln Gln Lys Pro Gly Gln Pro
        35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Thr Ile
 65                  70                  75                  80

Ser Ser Leu Gln Ala Glu Asp Val Ala Val Tyr Tyr Cys Phe His Gly
                 85                  90                  95
```

-continued

Thr His Val Pro Tyr Thr Phe Gly Gly Gly Thr Lys Val Glu Ile Lys
                100                 105                 110

<210> SEQ ID NO 10
<211> LENGTH: 112
<212> TYPE: PRT
<213> ORGANISM: Artificial Sequence
<220> FEATURE:
<223> OTHER INFORMATION: Synthetic Construct

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Thr Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe His Gly
                85                  90                  95

Thr His Val Pro Tyr Thr Phe Gly Gly Gly Thr Lys Val Glu Ile Lys
                100                 105                 110

<210> SEQ ID NO 11
<211> LENGTH: 112
<212> TYPE: PRT
<213> ORGANISM: Artificial Sequence
<220> FEATURE:
<223> OTHER INFORMATION: Synthetic Construct

<400> SEQUENCE: 11

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe His Gly
                85                  90                  95

Thr His Val Pro Tyr Thr Phe Gly Gly Gly Thr Lys Leu Glu Ile Lys
                100                 105                 110

<210> SEQ ID NO 12
<211> LENGTH: 444
<212> TYPE: PRT
<213> ORGANISM: Artificial Sequence
<220> FEATURE:
<223> OTHER INFORMATION: Synthetic Construct

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Ala
            20                  25                  30

```
Tyr Ile Asn Trp Val Arg Gln Ala Pro Gly Gln Gly Leu Glu Trp Met
            35                  40                  45
Gly Trp Ile Trp Pro Gly Pro Val Ile Thr Tyr Tyr Asn Pro Lys Phe
    50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Arg Glu Val Leu Ser Pro Phe Ala Tyr Trp Gly Gln Gly Thr
            100                 105                 110
Thr Val Thr Val Ser Ser Ala Ser Thr Lys Gly Pro Ser Val Phe Pro
        115                 120                 125
Leu Ala Pro Cys Ser Arg Ser Thr Ser Glu Ser Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Lys Thr Tyr Thr Cys Asn Val Asp His Lys Pro Ser
        195                 200                 205
Asn Thr Lys Val Asp Lys Arg Val Glu Ser Lys Tyr Gly Pro Pro Cys
        210                 215                 220
Pro Pro Cys Pro Ala Pro Glu Ala Ala Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser Gln Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Tyr Arg Val Val Ser Val Leu
        290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly
        435                 440
```

```
<210> SEQ ID NO 13
<211> LENGTH: 219
<212> TYPE: PRT
<213> ORGANISM: Artificial Sequence
<220> FEATURE:
<223> OTHER INFORMATION: Synthetic Construct

<400> SEQUENCE: 13

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Val His Ser
            20                  25                  30

Thr Gly Asn Thr Tyr Leu Glu Trp Tyr Gln Gln Lys Pro Gly Gln Pro
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Phe His Gly
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 14
<211> LENGTH: 219
<212> TYPE: PRT
<213> ORGANISM: Artificial Sequence
<220> FEATURE:
<223> OTHER INFORMATION: Synthetic Construct

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Thr Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe His Gly
                85                  90                  95

Thr His Val Pro Tyr Thr Phe Gly Gly Gly Thr Lys Val Glu Ile Lys
```

```
                    100                 105                 110
Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 15
<211> LENGTH: 354
<212> TYPE: DNA
<213> ORGANISM: Artificial Sequence
<220> FEATURE:
<223> OTHER INFORMATION: Synthetic Construct

<400> SEQUENCE: 15
caggtgcagc tggtgcagtc tggggctgag gtgaagaagc ctgggtcctc agtgaaggtt      60
tcctgcaagg catctggcta caccttcact gacgcgtata aaactgggt gcgacaggcc     120 cctggacaag gcttgagtg atgggatgg atttggcctg acccgttat tacttactac       180 aatccgaagt tcaagggcag agtcaccatt accgcggaca atccacgag cacagcctac    240 atggagctga gcagcctgag atctgaggac acggccgtgt attactgtgc gagaagggaa    300
gtactatccc cgtttgctta ctggggccaa ggaaccacgg tcaccgtctc ctca          354

<210> SEQ ID NO 16
<211> LENGTH: 336
<212> TYPE: DNA
<213> ORGANISM: Artificial Sequence
<220> FEATURE:
<223> OTHER INFORMATION: Synthetic Construct

<400> SEQUENCE: 16
gacatcgtga tgacccagtc tccagactcc ctggctgtgt ctctgggcga gagggccacc     60
atcaactgca gatctagtca gagcattgta catagtactg gaaacaccta tttagaatgg    120
taccagcaga aaccaggaca gcctcctaag ctgctcattt acaaagtttc caaccgattt    180
tctggggtcc ctgaccgatt cagtggcagc gggtctggga cagatttcac tctcaccatc    240
agcagcctgc aggctgaaga tgtggcagtt tattactgtt ttcacggcac tcatgttccg    300
tacacgttcg gcggagggac caaggtggag atcaaa                              336

<210> SEQ ID NO 17
<211> LENGTH: 336
<212> TYPE: DNA
<213> ORGANISM: Artificial Sequence
<220> FEATURE:
<223> OTHER INFORMATION: Synthetic Construct

<400> SEQUENCE: 17
gacatccaga tgacccagtc tccatcctct ctgtctgcat ctgtaggaga cagagtcacc     60
atcacttgca gatctagtca gagcattgta catagtactg gaaacaccta tttagaatgg    120
```

```
tatcagcaga aaccagggaa agccccctaag ctcctgatct ataaagtttc caaccgattt    180
tctggggtcc catcaaggtt cagtggcagt ggatctggga cagatttcac tctcaccatc    240
agcagtctgc aacctgaaga ttttgcaact tactactgtt ttcacggcac tcatgttccg    300
tacacgttcg gcggagggac caaggtggag atcaaa                              336
```

```
<210> SEQ ID NO 18
<211> LENGTH: 50
<212> TYPE: PRT
<213> ORGANISM: Homo sapiens

<400> SEQUENCE: 18
```

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
            20                  25                  30

Val Cys His Ser Gly Tyr Val Gly Ala Arg Cys Glu His Ala Asp Leu
        35                  40                  45

Leu Ala
    50

```
<210> SEQ ID NO 19
<211> LENGTH: 50
<212> TYPE: PRT
<213> ORGANISM: Mus musculus

<400> SEQUENCE: 19
```

Val Val Ser His Phe Asn Lys Cys Pro Asp Ser His Thr Gln Tyr Cys
1               5                   10                  15

Phe His Gly Thr Cys Arg Phe Leu Val Gln Glu Glu Lys Pro Ala Cys
            20                  25                  30

Val Cys His Ser Gly Tyr Val Gly Val Arg Cys Glu His Ala Asp Leu
        35                  40                  45

Leu Ala
    50

```
<210> SEQ ID NO 20
<211> LENGTH: 50
<212> TYPE: PRT
<213> ORGANISM: Rattus norvegicus

<400> SEQUENCE: 20
```

Val Val Ser His Phe Asn Lys Cys Pro Asp Ser His Thr Gln Tyr Cys
1               5                   10                  15

Phe His Gly Thr Cys Arg Phe Leu Val Gln Glu Glu Lys Pro Ala Cys
            20                  25                  30

Val Cys His Ser Gly Tyr Val Gly Val Arg Cys Glu His Ala Asp Leu
        35                  40                  45

Leu Ala
    50

```
<210> SEQ ID NO 21
<211> LENGTH: 50
<212> TYPE: PRT
<213> ORGANISM: Macaca fascicularis

<400> SEQUENCE: 21
```

Val Val Ser His Phe Asn Asp Cys Pro Asp Ser His Thr Gln Phe Cys
1               5                   10                  15

```
Phe His Gly Thr Cys Arg Phe Leu Val Gln Glu Asp Lys Pro Ala Cys
            20                  25                  30
Val Cys His Ser Gly Tyr Val Gly Ala Arg Cys Glu His Ala Asp Leu
            35                  40                  45
Leu Ala
    50
```

<210> SEQ ID NO 22
<211> LENGTH: 47
<212> TYPE: PRT
<213> ORGANISM: Artificial Sequence
<220> FEATURE:
<223> OTHER INFORMATION: Mature Human Epiregulin with addition of N-
      terminal methionine

<400> SEQUENCE: 22

```
Met Val Ser Ile Thr Lys Cys Ser Ser Asp Met Asn Gly Tyr Cys Leu
1               5                   10                  15
His Gly Gln Cys Ile Tyr Leu Val Asp Met Ser Gln Asn Tyr Cys Arg
            20                  25                  30
Cys Glu Val Gly Tyr Thr Gly Val Arg Cys Glu His Phe Phe Leu
            35                  40                  45
```

<210> SEQ ID NO 23
<211> LENGTH: 47
<212> TYPE: PRT
<213> ORGANISM: Artificial Sequence
<220> FEATURE:
<223> OTHER INFORMATION: Mature Mouse (Mus musculus) Epiregulin with
      addition of N-terminal methionine

<400> SEQUENCE: 23

```
Met Val Gln Ile Thr Lys Cys Ser Ser Asp Met Asp Gly Tyr Cys Leu
1               5                   10                  15
His Gly Gln Cys Ile Tyr Leu Val Asp Met Arg Glu Lys Phe Cys Arg
            20                  25                  30
Cys Glu Val Gly Tyr Thr Gly Leu Arg Cys Glu His Phe Phe Leu
            35                  40                  45
```

<210> SEQ ID NO 24
<211> LENGTH: 46
<212> TYPE: PRT
<213> ORGANISM: Macaca fascicularis

<400> SEQUENCE: 24

```
Val Ser Ile Thr Lys Cys Asn Ser Asp Met Asn Gly Tyr Cys Leu His
1               5                   10                  15
Gly Gln Cys Ile Tyr Leu Val Asp Met Ser Gln Asn Tyr Cys Arg Cys
            20                  25                  30
Glu Val Gly Tyr Thr Gly Val Arg Cys Glu His Phe Tyr Leu
            35                  40                  45
```

<210> SEQ ID NO 25
<211> LENGTH: 72
<212> TYPE: PRT
<213> ORGANISM: Homo sapiens

<400> SEQUENCE: 25

```
Ala Val Thr Val Thr Pro Pro Ile Thr Ala Gln Ala Asp Asn Ile
1               5                   10                  15
Glu Gly Pro Ile Ala Leu Lys Phe Ser His Leu Cys Leu Glu Asp His
            20                  25                  30
```

```
Asn Ser Tyr Cys Ile Asn Gly Ala Cys Ala Phe His His Glu Leu Glu
        35                  40                  45

Lys Ala Ile Cys Arg Cys Phe Thr Gly Tyr Thr Gly Glu Arg Cys Glu
 50                  55                  60

His Leu Thr Leu Thr Ser Tyr Ala
 65                  70

<210> SEQ ID NO 26
<211> LENGTH: 51
<212> TYPE: PRT
<213> ORGANISM: Mus musculus

<400> SEQUENCE: 26

Leu Lys Phe Ser His Pro Cys Leu Glu Asp His Asn Ser Tyr Cys Ile
 1               5                  10                  15

Asn Gly Ala Cys Ala Phe His His Glu Leu Lys Gln Ala Ile Cys Arg
            20                  25                  30

Cys Phe Thr Gly Tyr Thr Gly Gln Arg Cys Glu His Leu Thr Leu Thr
        35                  40                  45

Ser Tyr Ala
     50

<210> SEQ ID NO 27
<211> LENGTH: 54
<212> TYPE: PRT
<213> ORGANISM: Artificial Sequence
<220> FEATURE:
<223> OTHER INFORMATION: Mature Human EGF with addition of N-terminal
      methionine

<400> SEQUENCE: 27

Met Asn Ser Asp Ser Glu Cys Pro Leu Ser His Asp Gly Tyr Cys Leu
 1               5                  10                  15

His Asp Gly Val Cys Met Tyr Ile Glu Ala Leu Asp Lys Tyr Ala Cys
            20                  25                  30

Asn Cys Val Val Gly Tyr Ile Gly Glu Arg Cys Gln Tyr Arg Asp Leu
        35                  40                  45

Lys Trp Trp Glu Leu Arg
     50

<210> SEQ ID NO 28
<211> LENGTH: 86
<212> TYPE: PRT
<213> ORGANISM: Homo sapiens

<400> SEQUENCE: 28

Asp Leu Gln Glu Ala Asp Leu Asp Leu Leu Arg Val Thr Leu Ser Ser
 1               5                  10                  15

Lys Pro Gln Ala Leu Ala Thr Pro Asn Lys Glu Glu His Gly Lys Arg
            20                  25                  30

Lys Lys Lys Gly Lys Gly Leu Gly Lys Lys Arg Asp Pro Cys Leu Arg
        35                  40                  45

Lys Tyr Lys Asp Phe Cys Ile His Gly Glu Cys Lys Tyr Val Lys Glu
     50                  55                  60

Leu Arg Ala Pro Ser Cys Ile Cys His Pro Gly Tyr His Gly Glu Arg
 65                  70                  75                  80

Cys His Gly Leu Ser Leu
                 85

<210> SEQ ID NO 29
```

```
<211> LENGTH: 80
<212> TYPE: PRT
<213> ORGANISM: Homo sapiens

<400> SEQUENCE: 29

Asp Gly Asn Ser Thr Arg Ser Pro Glu Thr Asn Gly Leu Leu Cys Gly
1               5                   10                  15

Asp Pro Glu Glu Asn Cys Ala Ala Thr Thr Thr Gln Ser Lys Arg Lys
            20                  25                  30

Gly His Phe Ser Arg Cys Pro Lys Gln Tyr Lys His Tyr Cys Ile Lys
        35                  40                  45

Gly Arg Cys Arg Phe Val Val Ala Glu Gln Thr Pro Ser Cys Val Cys
    50                  55                  60

Asp Glu Gly Tyr Ile Gly Ala Arg Cys Glu Arg Val Asp Leu Phe Tyr
65                  70                  75                  80

<210> SEQ ID NO 30
<211> LENGTH: 98
<212> TYPE: PRT
<213> ORGANISM: Homo sapiens

<400> SEQUENCE: 30

Ser Val Arg Val Glu Gln Val Val Lys Pro Pro Gln Asn Lys Thr Glu
1               5                   10                  15

Ser Glu Asn Thr Ser Asp Lys Pro Lys Arg Lys Lys Lys Gly Gly Lys
            20                  25                  30

Asn Gly Lys Asn Arg Arg Asn Arg Lys Lys Lys Asn Pro Cys Asn Ala
        35                  40                  45

Glu Phe Gln Asn Phe Cys Ile His Gly Glu Cys Lys Tyr Ile Glu His
    50                  55                  60

Leu Glu Ala Val Thr Cys Lys Cys Gln Gln Glu Tyr Phe Gly Glu Arg
65                  70                  75                  80

Cys Gly Glu Lys Ser Met Lys Thr His Ser Met Ile Asp Ser Ser Leu
                85                  90                  95

Ser Lys

<210> SEQ ID NO 31
<211> LENGTH: 442
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Ala
            20                  25                  30

Tyr Ile Asn Trp Val Lys Gln Arg Pro Gly Gln Gly Leu Glu Trp Ile
        35                  40                  45

Gly Trp Ile Trp Pro Gly Pro Val Ile Thr Tyr Asn Pro Lys Phe
    50                  55                  60

Lys Gly Lys Ala Thr Leu Thr Val Asp Lys Ser Ser Ser Thr Ala Tyr
65                  70                  75                  80

Met Leu Leu Ser Ser Leu Thr Ser Glu Asp Ser Ala Phe Tyr Phe Cys
                85                  90                  95

Ala Arg Arg Glu Val Leu Ser Phe Ala Tyr Trp Gly Gln Gly Thr
            100                 105                 110
```

```
Leu Val Thr Val Ser Ala Ala Lys Thr Thr Pro Pro Ser Val Tyr Pro
            115                 120                 125

Leu Ala Pro Gly Ser Ala Ala Gln Thr Asn Ser Met Val Thr Leu Gly
        130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Val Thr Val Pro Ser Ser Thr
                180                 185                 190

Trp Pro Ser Glu Thr Val Thr Cys Asn Val Ala His Pro Ala Ser Ser
            195                 200                 205

Thr Lys Val Asp Lys Lys Ile Val Pro Arg Asp Cys Gly Cys Lys Pro
        210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440

<210> SEQ ID NO 32
<211> LENGTH: 219
<212> TYPE: PRT
<213> ORGANISM: Artificial Sequence
<220> FEATURE:
<223> OTHER INFORMATION: Synthetic Construct

<400> SEQUENCE: 32

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
```

```
                35                   40                  45
Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe His Gly
                85                  90                  95

Thr His Val Pro Tyr Thr Phe Gly Gly Gly Thr Lys Leu Glu Ile Lys
                100                 105                 110

Arg Ala Asp Ala Ala Pro Thr Val Ser Ile Phe Pro Pro Ser Ser Glu
                115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
                195                 200                 205

Pro Ile Val Lys Ser Phe Asn Arg Asn Glu Cys
        210                 215

<210> SEQ ID NO 33
<211> LENGTH: 46
<212> TYPE: PRT
<213> ORGANISM: Homo sapiens

<400> SEQUENCE: 33

Val Ser Ile Thr Lys Cys Ser Ser Asp Met Asn Gly Tyr Cys Leu His
1               5                   10                  15

Gly Gln Cys Ile Tyr Leu Val Asp Met Ser Gln Asn Tyr Cys Arg Cys
                20                  25                  30

Glu Val Gly Tyr Thr Gly Val Arg Cys Glu His Phe Phe Leu
                35                  40                  45
```